(12) United States Patent
Zambaux

(10) Patent No.: US 7,431,494 B2
(45) Date of Patent: Oct. 7, 2008

(54) FLEXIBLE MIXING BAG FOR MIXING SOLIDS, LIQUIDS, AND GASES

(75) Inventor: Jean-Pascal Zambaux, Allonzier la Caille (FR)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 11/831,735

(22) Filed: Jul. 31, 2007

(65) Prior Publication Data

US 2008/0031082 A1 Feb. 7, 2008

Related U.S. Application Data

(63) Continuation of application No. 10/684,932, filed on Oct. 14, 2003, now Pat. No. 7,249,880.

(51) Int. Cl.
*B01F 15/00* (2006.01)
*B01F 13/06* (2006.01)
*B01F 15/02* (2006.01)
*B01F 15/06* (2006.01)
*B01F 7/18* (2006.01)
*B65D 30/10* (2006.01)

(52) U.S. Cl. ............ 366/144; 366/145; 366/194; 366/277; 366/279; 366/331; 366/348; 366/349

(58) Field of Classification Search .......... 366/276, 366/277, 278, 279, 349, 144, 145, 194, 348, 366/184, 331; 383/127, 105, 121
See application file for complete search history.

(56) References Cited

U.S. PATENT DOCUMENTS

| | | | |
|---|---|---|---|
| 2,877,994 A | 3/1959 | Jones | |
| 3,010,303 A | 11/1961 | Bochan | |
| 3,384,354 A | 5/1968 | Migule et al. | |
| 3,572,651 A | 3/1971 | Harker | |
| 3,647,397 A | 3/1972 | Coleman | |
| 3,802,470 A | 4/1974 | Coleman | |
| 4,112,518 A | 9/1978 | Garlinghouse | |
| 5,002,890 A | 3/1991 | Morrison | |
| 5,193,977 A | 3/1993 | Dame | |
| 5,362,642 A | 11/1994 | Kern | |
| 5,456,586 A | 10/1995 | Carson | |
| 5,633,165 A | 5/1997 | Swartz | |
| 5,941,635 A | 8/1999 | Stewart | |
| 5,988,422 A | 11/1999 | Vallot | |
| 6,071,005 A | 6/2000 | Ekambaram et al. | |
| 6,077,356 A | 6/2000 | Bouchard | |
| 6,178,925 B1 | 1/2001 | Sturm | |
| 6,186,932 B1 | 2/2001 | Vallot | |
| 6,494,613 B2 | 12/2002 | Terentiev | |

(Continued)

*Primary Examiner*—Tony G Soohoo
(74) *Attorney, Agent, or Firm*—Vincent K. Gustafson; Intellectual Property Technology Law

(57) ABSTRACT

In an embodiment, an apparatus includes a disposable and flexible mixing tank, configurable as a bag, having a sealed sleeve therein for arrangement of a mixing device. The volume of the mixing tank is defined by an inner wall of the mixing tank and an inner wall of the sleeve. The mixing tank may be used to mix, store, reconstitute and/or dispense materials therein. Draining of a mixture may be aided with pressurized gas. Heating or cooling of the contents of a mixing tank may be accomplished with a thermal exchange fluid disposed within a thermal exchange vessel and in thermal communication with the tank.

36 Claims, 10 Drawing Sheets

U.S. PATENT DOCUMENTS

| | | |
|---|---|---|
| 6,634,783 B2 | 10/2003 | Baron |
| 6,670,171 B2 | 12/2003 | Carll |
| 6,837,610 B2 | 1/2005 | Cadogan et al. |
| 6,844,186 B2 | 1/2005 | Carll |
| 7,025,234 B2 | 4/2006 | Priebe |
| 7,249,880 B2 * | 7/2007 | Zambaux .................. 366/277 |
| 2001/0039369 A1 | 11/2001 | Terentiev |
| 2002/0105856 A1 | 8/2002 | Terentiev |
| 2003/0226857 A1 | 12/2003 | Bibbo et al. |
| 2003/0231546 A1 | 12/2003 | Bibbo et al. |
| 2004/0027912 A1 | 2/2004 | Bibbo et al. |
| 2004/0062140 A1 | 4/2004 | Cadogan et al. |
| 2005/0002274 A1 | 1/2005 | Terentiev |
| 2005/0078552 A1 | 4/2005 | Zambaux |
| 2005/0239199 A1 | 10/2005 | Kunas et al. |
| 2008/0031082 A1 * | 2/2008 | Zambaux .................. 366/139 |

* cited by examiner

FLEXIBLE MIXING BAG FOR MIXING SOLIDS, LIQUIDS, AND GASES

CROSS REFERENCE TO RELATED APPLICATIONS

This is a continuation of U.S. patent application Ser. No. 10/684,932 filed on Oct. 14, 2003, and issued as U.S. Pat. No. 7,249,880 on Jul. 31, 2007. The disclosures of the foregoing application and patent are hereby incorporated herein in their respective entireties for all purposes, and the priority of such application is hereby claimed under the provisions of 35 U.S.C. § 120.

FIELD OF THE INVENTION

The mixing of components, such as different types of solids, liquids and/or gases, has a number of applications in different industries. For example, in the pharmaceutical industry, different types of drugs are mixed together. In the medical field, body fluids (such as blood) and/or drugs are typical components that are mixed. In the semiconductor field, wet solutions are combined with abrasives to make slurries. The food industry also incorporates mixing operations into a number of applications. For example, water is mixed with dehydrated food for the rehydration of such food.

However, in these and other industries, the components that are mixed may be hazardous, dangerous, infectious and/or require high levels of purity. For example, in the pharmaceutical and/or medical industries, the components that are to be mixed may be toxic. Additionally, in a number of situations, the handling of powders may be dangerous because of the possibilities of inhalation of such powders. In the medical field, individuals that handle body fluids, such as fluids that are HIV-infected, do so while attempting to avoid direct contact with these fluids. Furthermore, in the semiconductor industry, handling of chemicals is avoided to reduce the potential for forming particulate and introducing impurities.

Conventional mixing devices generally involve a glass tank for components that are of small volumes and a stainless steel tank for components of larger volumes. These tanks often include a screw to agitate and maintain powders within suspension. Such screws are also used to homogenize multiphase solutions. Prior to use, these mixing tanks must be washed and sterilized. Typically, an autoclave is used for washing and sterilizing small volume tanks, while a water steam-based operation is employed for washing and sterilizing larger volume tanks. When preparing batches of post-etch residue removers for semiconductor applications, introduction of contaminants must be excluded at all levels of processing to decrease particulate formation, which leads to device failure. These wash, sterilize, and process operations, which are essential to the specified technologies, are typically time-consuming and expensive, and require highly qualified individuals for their performance. Further, periodic maintenance of mixing devices associated with the various technologies must be performed to ensure proper operation. In certain cases, washing/sterilizing operations as well as the maintenance of these mixing devices may represent more than a third of the total cost of operating and maintaining such mixing devices, which may be prohibitively expensive for given applications. Additionally, mixing of components may cause the pressure to increase within these conventional mixing devices. If this increased pressure is not accounted for, then the mixing of such components may become dangerous, such as the possibility that the tanks could break apart/explode due to this internal pressure. Moreover, with the use of many mixing devices currently employed to mix pharmaceuticals, the displacement of some pharmaceutical outside the mixing device cannot be eliminated, and therefore the amount of pharmaceutical remaining inside the mixing device, after mixing, may not be sufficiently accurate or precisely known. This is problematic when the FDA requires the administration of such a pharmaceutical in precise, accurate and known quantities.

Due to their multiple advantages, disposable containers are becoming increasingly useful in many industrial applications, particularly as storage containers.

In biological processing, there is an ever-increasing need for disposable products, such as storage bags, which can range in size from 10 to more than 3,000 liters. Current uses include, among others, storage of products or components awaiting disposition to further processing steps such as, for example, purification. Often, however, the stored products or components are mixtures, which, over time, may separate out into phases or components. Emulsions and suspensions, for example, are particularly predisposed to such phase separations.

Current industry standards require remixing, regeneration and/or revalidation of a suspension or emulsion before further processing can resume. In order for remixing to occur without removing the contents from a storage bag, a magnetic stir bar is used. Often, the duration of the regeneration/revalidation step is up to several hours, and the quality of mixing is not good. Additionally, such a process is prone to particle generation inside the bag that contaminates the formulation therein.

Alternatively, a recirculation loop may be employed to regenerate mixtures, such as emulsions or suspensions, whereby liquid separated from the bulk mixture is repeatedly drained from the foot or base of the storage bag and refilled through the top of the bag. In addition to being time-consuming, such an alternative process requires the container to be opened and resealed.

As noted above, mixing of materials continues to face challenges in many industrial applications. Therefore, a system having both storage and mixing capabilities, and that uses disposable elements, is needed. The system should offer reduced labor, lower production costs, and improved product quality in mixing applications.

SUMMARY OF THE INVENTION

The present invention relates to a disposable mixing and storage bag. More particularly, the present invention relates to a disposable bag, useful for mixing, storing, reconstituting and/or dispensing materials.

In one aspect, the invention relates to a mixing apparatus comprising: a hollow mixing container having at least one interior wall; a mixing paddle adapted to engage a support rod mechanically coupleable to receive kinetic energy from a kinetic energy source, the mixing paddle having at least one widened paddle portion that is wider than a nominal diameter or cross-sectional width of the support rod; a coupling guide joined to the mixing container, the coupling guide defining an aperture sized to permit pivotal arrangement of the support rod between the kinetic energy source and the mixing container; an integral sleeve sealingly and permanently welded proximate the coupling guide aperture to any of the container and the coupling guide, the sleeve having a closed end protruding into the interior of the hollow container, having at least one exterior wall, and defining a cavity containing the mixing paddle, the cavity having at least one widened cavity portion disposed about the at least one widened paddle portion; a drain port associated with the mixing container; and at least one inlet port associated with the mixing container; wherein (i) the at least one interior wall of the mixing container and the at least one exterior wall of the sleeve encloses a volume, (ii) the sleeve serves as an isolation barrier between the volume and the mixing paddle, and (iii) the mixing container is adapted to permit pressure-assisted draining of any contents thereof.

In another aspect, the invention relates to a mixing method employing a mixing apparatus including (i) a kinetic energy source, (ii) a hollow mixing bag having a flexible integral sleeve joined thereto with a closed end of the sleeve protruding into the mixing bag, and having an associated drain port and an associated at least one inlet port, and (iii) a mixing paddle enveloped by the sleeve and adapted to receive a support rod coupleable to the kinetic energy source, wherein at least one interior wall of the bag and an exterior wall of the sleeve defines an interior volume, and the sleeve serves as an isolation barrier between the interior volume and the mixing paddle, the method comprising the steps of: supplying at least two components of a mixture to the interior volume; engaging the support rod between the kinetic energy source and the mixing paddle; mixing the at least two components by moving the enveloped mixing paddle in a closed curvilinear path within the interior volume without continuous rotation of the support rod about a longitudinal axis defined by the support rod to combine the at least two components and form said mixture; supplying pressurized gas to the container via any inlet port of the at least one inlet port; and draining at least a portion of said mixture via said drain port.

In another aspect, the invention relates to a mixing apparatus comprising: a hollow mixing container having at least one interior wall; a mixing paddle adapted to engage a support rod mechanically coupleable to receive kinetic energy from a kinetic energy source, the mixing paddle having at least one widened paddle portion that is wider than a nominal diameter or cross-sectional width of the support rod; a coupling guide joined to the mixing container, the coupling guide defining an aperture sized to permit pivotal arrangement of the support rod between the kinetic energy source and the mixing container; an integral sleeve sealingly and permanently welded proximate the coupling guide aperture to any of the container and the coupling guide, the sleeve having a closed end protruding into the interior of the hollow container, having at least one exterior wall, and defining a cavity containing the mixing paddle, the cavity having at least one widened cavity portion disposed about the at least one widened paddle portion; a thermal exchange vessel arranged to contain a thermal exchange fluid in thermal communication with at least a portion of the mixing container; and a thermal exchange element disposed in at least intermittent thermal communication with the thermal exchange fluid; wherein the at least one interior wall of the mixing container and the at least one exterior wall of the sleeve encloses a volume, and the sleeve serves as an isolation barrier between the volume and the mixing paddle.

In another aspect, the invention relates to a material processing method employing a mixing apparatus including (i) a kinetic energy source, (ii) a hollow mixing bag having a flexible integral sleeve joined thereto with a closed end of the sleeve protruding into the mixing bag, and (iii) a mixing paddle enveloped by the sleeve and adapted to receive a support rod coupleable to the kinetic energy source, wherein at least one interior wall of the bag and an exterior wall of the sleeve defines an interior volume, and the sleeve serves as an isolation barrier between the interior volume and the mixing paddle, and (iv) a thermal exchange vessel arranged to contain a thermal exchange fluid in thermal communication with at least a portion of the mixing container, the method comprising the steps of: supplying at least two components of a mixture to the interior volume; engaging the support rod between the kinetic energy source and the mixing paddle; mixing the at least two components by moving the enveloped mixing paddle in a closed curvilinear path within the interior volume without continuous rotation of the support rod about a longitudinal axis defined by the support rod to combine the at least two components and form said mixture; and controlling temperature of said mixture by altering any of temperature and circulation of said thermal exchange fluid.

Other aspects, features and embodiments of the invention will be more fully apparent from the ensuing disclosure and appended claims.

BRIEF DESCRIPTION OF THE DRAWINGS

Embodiments of the invention may be best understood by referring to the following description and accompanying drawings, which illustrate such embodiments. The numbering scheme for the Figures included herein are such that the leading number for a given reference number in a Figure is generally associated with the number of the Figure. For example, a flexible mixing tank 100 can be depicted in FIG. 1. However, reference numbers are the same for those elements that are the same across different Figures. In the drawings.

DETAILED DESCRIPTION OF THE INVENTION, AND PREFERRED EMBODIMENTS THEREOF

Figure 1:
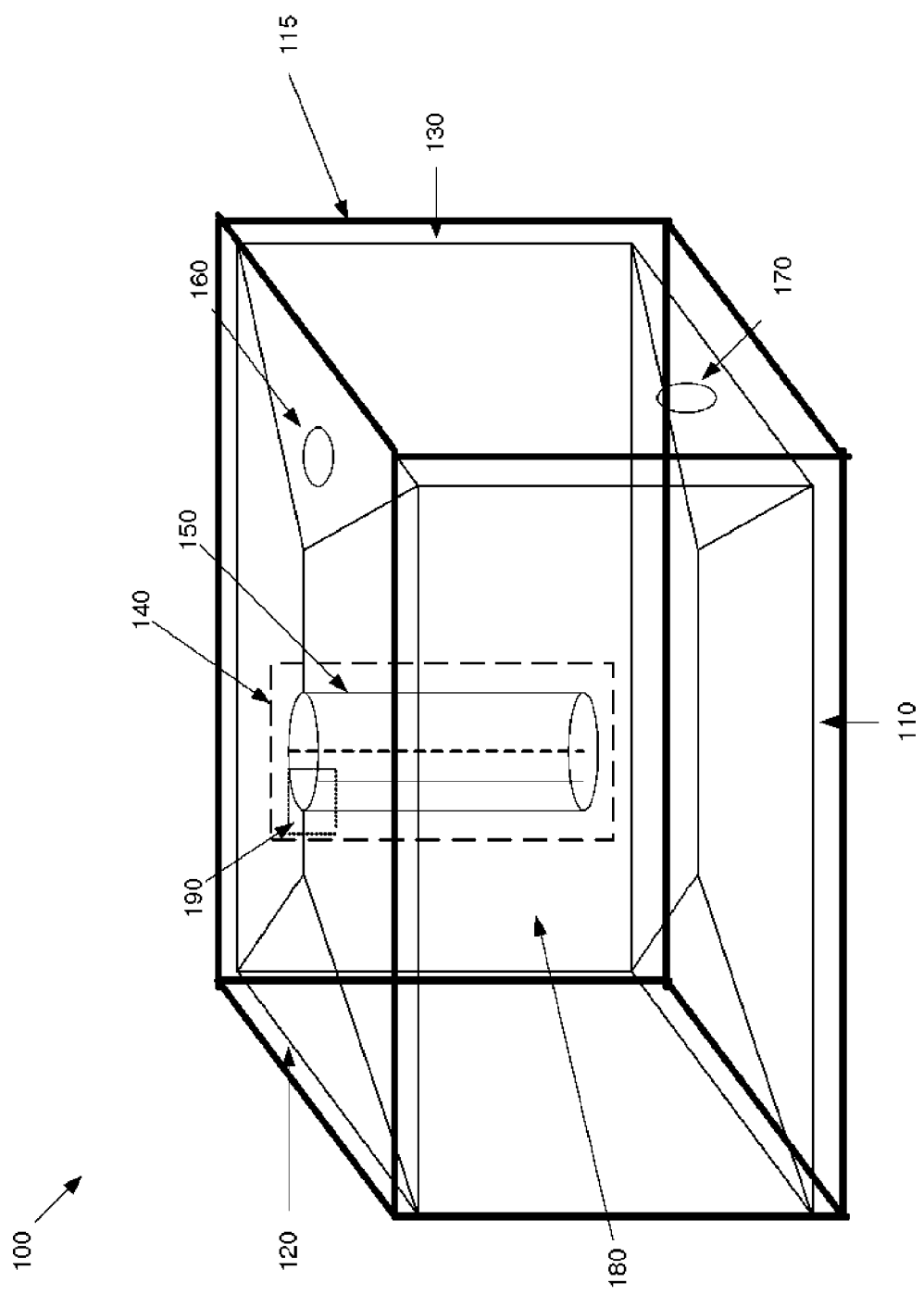
FIG. 1 illustrates a perspective view of a disposable mixing tank, according to one embodiment of the present invention.

The present invention is based on an apparatus, method, and system for mixing solids, liquids and/or gases, having the potential to reduce labor, lower production costs, and improve product quality in mixing applications. It allows disposable bags or tanks to be used to replace permanent mixing tanks in many laboratory and pilot scale operations, thus eliminating cleaning, sterilization, and product contamination concerns.

Embodiments of the invention are described to include a disposable and flexible mixing tank having a sealed sleeve arranged therein. The mixing tank and sleeve may be manufactured from any suitable material. In one embodiment, the mixing tank and sleeve are made of any suitable material having a property where upon removal of an extending force, it is capable of substantially recovering its original size and shape and/or exhibits a significant retractive force. As such, the mixing tank and sleeve may be made of any suitable type of stretchable, collapsible, pliable and/or elastic material. In a preferred embodiment, the disposable mixing tank is manufactured from a fully transparent film to allow for visual inspection of the tank's contents before and after use.

As used herein, the term "collapsible" refers to a material that may fold down into a more compact shape.

As used herein, the term "pliable" refers to a material that is supple or adjustable enough to bend freely without breaking.

As used herein, the term "elastic," or "elastomeric" refers to that property of a material where upon removal of an extending force, it is capable of substantially recovering its original size and shape and/or exhibits a significant retractive force.

As used herein, the term "stretch," or "stretchable" refers to a material that is either elastic or extensible. That is, the material is capable of being extended, deformed, or the like, without breaking, and may or may not significantly retract after removal of an extending force. In an embodiment, the stretchable material can optionally be biaxial stretchable.

As used herein, the term "biaxial stretch" or "biaxial stretchable" refers to a material having stretchability in two directions perpendicular to one another, e.g. stretchability in a machine direction and in a cross machine direction, or in a longitudinal direction (front to back) and a lateral direction (side to side).

The mixing tank and sleeve may be manufactured from any suitable material. Suitable materials include, e.g., films, polymers, thermoplastic polymers, homopolymers, copolymers, block copolymers, graft copolymers, random copolymers, alternating copolymers, terpolymers, metallocene polymers, nonwoven fabric, spunbonded fibers, meltblown fibers, polycellulose fibers, polyester fibers, polyurethane fibers, polyolefin fibers, polyamide fibers, cotton fibers, copolyester fibers, open cell foam, polyurethane, polyvinyl chloride, polyethylene, metals, alloys, fiberglass, glass, plastic (e.g., polyethylene (PE), polypropylene (PP), polyvinyl chloride (PVC), polyethylene terephtalate (PET), polyetheretherketone (PEEK) and polytetrafluoroethylene (PTFE) and polyfluoroalkoxy (PFA) derivates thereof), rubber, and combinations or mixtures thereof.

As used herein, the term "film" refers to a thermoplastic film made using a film extrusion and/or foaming process, such as a cast film or blown film extrusion process. For the purposes of the present invention, the term includes nonporous films as well as microporous films. Films may be vapor permeable or vapor impermeable, and function as liquid barriers under normal use conditions.

As used herein, the term "thermoplastic" refers to uncrosslinked polymers of a thermally sensitive material, which flow under the application of heat or pressure.

As used herein, the term "polymers" includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and atactic symmetries.

As used herein, the term "metallocene polymers" refers to those polymer materials that are produced by the polymerization of at least ethylene using metallocenes or constrained geometry catalysts, a class of organometallic complexes, as catalysts.

As used herein, the terms "nonwoven" and "nonwoven web" refer to fibrous materials and webs of fibrous material, which are formed without the aid of a textile weaving or knitting process.

As used herein, the term "spunbonded fibers" refers to small diameter fibers, which are formed by extruding molten thermoplastic material as filaments from a plurality of fine capillaries of a spinnerette having a circular or other configuration, with the diameter of the extruded filaments then being rapidly reduced.

As used herein, the term "meltblown fiber" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter (the average microfiber diameter is not greater than about 100 microns, for example, having an average diameter of from about 0.5 microns to about 50 microns, more particularly, microfibers may have an average diameter of from about 4 microns to about 40 microns).

References in the specification to "one embodiment", "an embodiment", "an example embodiment", etc., indicate that the embodiment described may include a particular feature, structure, or characteristic, but every embodiment need not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments, whether or not explicitly described.

Embodiments of the invention include features, methods or processes embodied within machine-executable instructions provided by a machine-readable medium. A machine-readable medium includes any mechanism, which provides (i.e., stores and/or transmits) information in a form accessible by a machine (e.g., a computer, a network device, a personal digital assistant, manufacturing tool, any device with a set of one or more processors, etc.). In an exemplary embodiment, a machine-readable medium includes volatile and/or non-volatile media (e.g., read only memory (ROM); random access memory (RAM); magnetic disk storage media; optical storage media; flash memory devices; etc.), as well as electrical, optical, acoustical or other forms of propagated signals (e.g., carrier waves, infrared signals, digital signals, etc.).

Such instructions are utilized to cause a general or special purpose processor, programmed with the instructions, to perform methods or processes of the embodiments of the invention. Alternatively, the features or operations of embodiments of the invention are performed by specific hardware components, which contain hard-wired logic for performing the operations, or by any combination of programmed data processing components and specific hardware components. Embodiments of the invention may be implemented with or include software, data processing hardware, data processing system-implemented methods, and various processing operations, further described herein.

The disposable mixing tank as described herein provides a closed system for use in all phases of processing, reconstitution or revalidation of mixtures. Preferably, the mixing tank is flexible. The mixing tank may be manufactured from pyrogen free, sterile materials, to reduce risks associated with cross contamination. The flexible bag may comprise one or more ports for filling, spiking, adding and/or draining components to reduce the amount of human contact with the various components (which may be hazardous, dangerous and/or infectious) that are to be mixed as part of and during the mixing of such components.

The present invention provides a disposable and flexible mixing tank having a sealed sleeve arranged therein. As a single-use apparatus, the mixing tank may be used to mix two or more components, and store any of the two or more components before or after mixing. Accordingly, the mixing tank may be discarded after a single use, thereby eliminating washing/sterilizing operations as well as maintenance associated with conventional mixing devices. Moreover, as will be described, in one embodiment, a number of inlet and outlet openings may be further incorporated into the mixing tank FIG. 1 illustrates a perspective view of a disposable mixing tank, 100, according to one embodiment of the present invention. The tank is useful for storing and/or mixing liquids, solids, and/or gases. The tank may have a volume of 5 liters or more, and be of a collapsible type that assumes a substantially parallelepiped shape when filled. A support frame 115 may support the mixing tank 100, to maintain a sufficient tension during loading of components into the mixing tank as well as during a mixing step. Mixing tank 100 comprises a bottom wall 110, a top wall 120, and four lateral walls 130. The mixing tank may further comprise inlet(s) 160 and optional outlet(s) 170. In particular, FIG. 1 illustrates a perspective view of a flexible mixing tank (apparatus/device) that includes a sealed sleeve or compartment 140, which is defined by wall 150. The sealed sleeve may be located on or attached to any wall of the mixing tank. Preferably, however, the sealed sleeve is arranged on the upper or top wall and centrally located.

The disposable mixing tank 100 may include any number of inlet openings 160 and outlet opening(s) 170. A more detailed description of the different components of the mixing tank 100 will be described below in conjunction with the description of the various components thereof.

The flexible mixing tank may be manufactured to assume any shape and volume when filled. Preferably, the shape of the mixing tank is cylindrical or parallelepiped and the volume is between 5 and 10,000 liters. More preferably, the volume of the flexible mixing tank is between about 10 and 3000 liters.

Figure 2:
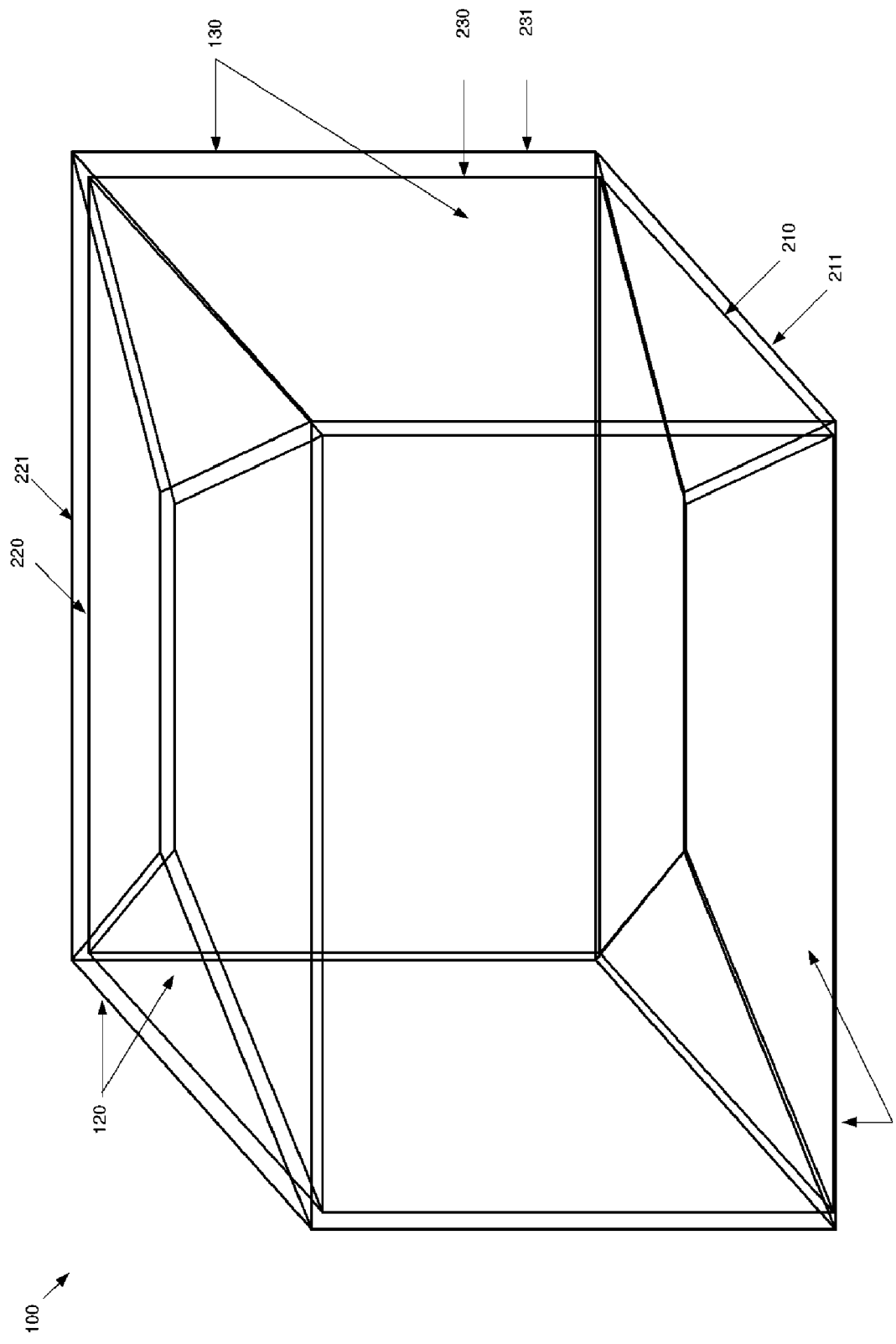
FIG. 2 illustrates a perspective view of the substantially parallelepiped shaped mixing tank of FIG. 1.

FIG. 2 illustrates a perspective view of the substantially parallelepiped shaped mixing tank of FIG. 1. The bottom, top, and lateral walls, 110, 120 and 130 respectively, having interior portions, 210, 220 and 230 respectively, and having exterior portions, 211, 221, 231, respectively, may be of any suitable thickness readily determined by one skilled in the art. Moreover, each wall may be manufactured from one or more of the same or different materials. Moreover, each wall may be manufactured from one or more of the same or different materials.

Figure 3B:
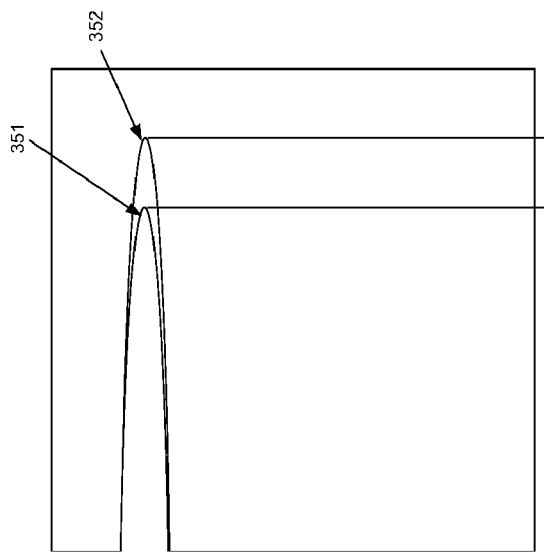
FIG. 3B illustrates a perspective view of an expanded portion, of the substantially cylindrical sealed sleeve 140 of the mixing tank of FIG. 1.
Figure 3A:
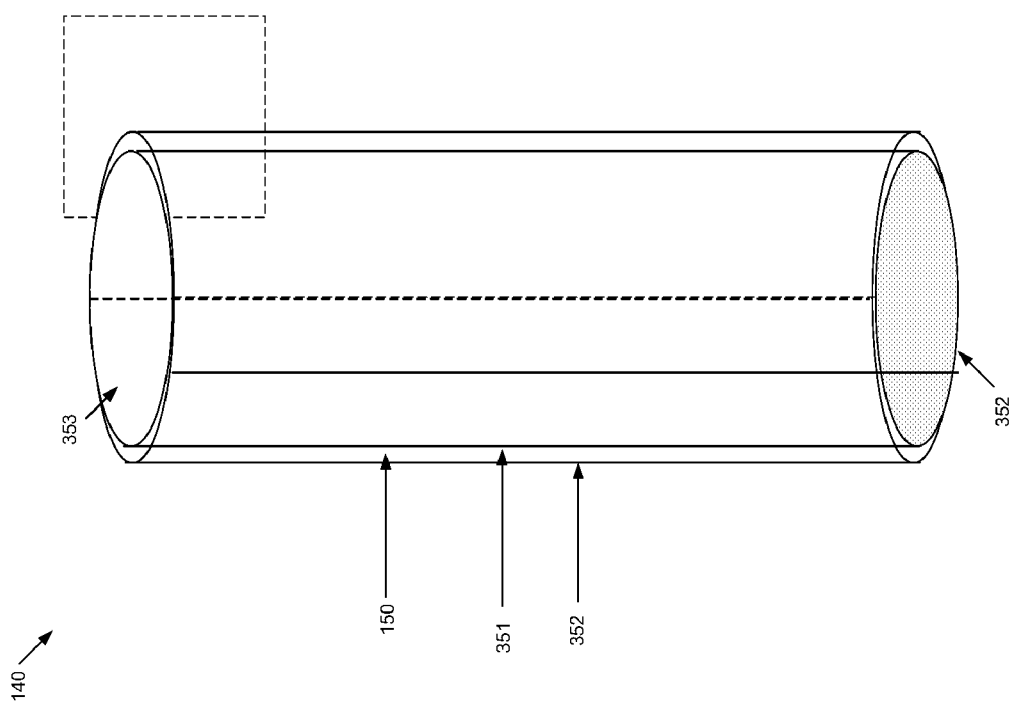
FIG. 3A illustrates a perspective view.

FIGS. 3A and 3B illustrate perspective views of the substantially cylindrical sealed sleeve 140 of the mixing tank of FIG. 1, and an expanded portion thereof, respectively. The wall 150 of sealed sleeve 140, having both an interior portion 351, and an exterior portion 352, respectively, may be manufactured from materials that are the same as or different from the mixing tank walls. When the sleeve 140 of FIG. 3A is joined to the tank 100 of FIG. 2, the interior portions 210, 220, 230 of mixing tank walls 110, 120, 130 and the exterior portion 352 of the sealed sleeve 140 together define an interior volume 180 of mixing tank 100, configured to house components of a mixture, before or after a mixing process.

The sealed sleeve 140 may be of any suitable thickness readily determined by one skilled in the art. Moreover, the sealed sleeve, 140, may comprise multiple sections, such as side wall(s) or a single article of manufacture.

The sleeve 140, which is preferably flexible, is sealably coupled to the disposable mixing tank 100 at a seam or juncture 190 by any process readily available to one skilled in the art, including, but not limited to, joining, welding, heat shrinking, shrink down plastic tubing, or combinations thereof. A sleeve cavity 353 is defined by the interior portion of sleeve wall 351, and has length or height and diameter or width dimensions. The sleeve may be of a regular or irregular shape (i.e., cylindrical vs. tapered, respectively). Moreover, the sleeve may be form fitting so as to directly contact an object arranged therein, much like a hand in a glove.

The sleeve may define a sealed passageway for insertion or arrangement of mixing means therein. The mixing means is isolated from the interior of the mixing tank, by the sleeve wall and hence does not contact the interior of the tank 180 or components therein. The mixing means, which when placed in a mixing mode, serves to mix components in the tank. The mixing means serves to create turbulence and accomplish mixing while presenting no risk of contact with the mixture inside the vessel.

Figure 4A:
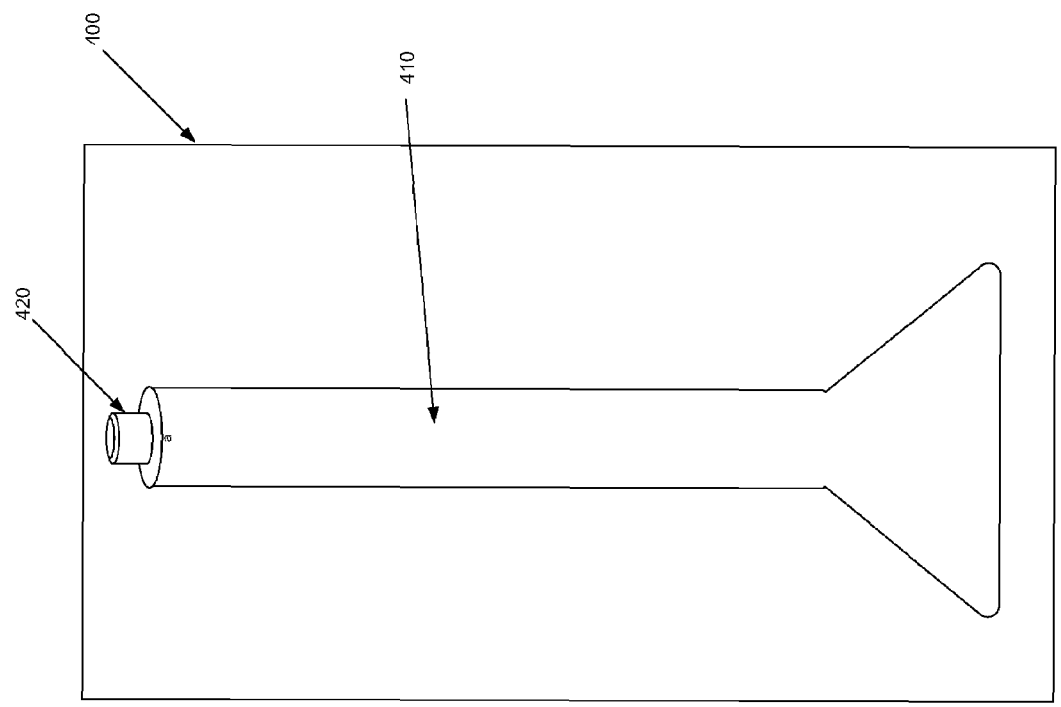
FIGS. 4A-4C illustrate perspective views of: a disposable mixing tank and mixing means arranged separately; mixing means fully inserted into the disposable mixing tank; and mixing means partially inserted into the disposable mixing tank, respectively, according to a further embodiment of the present invention.
Figure 4A:
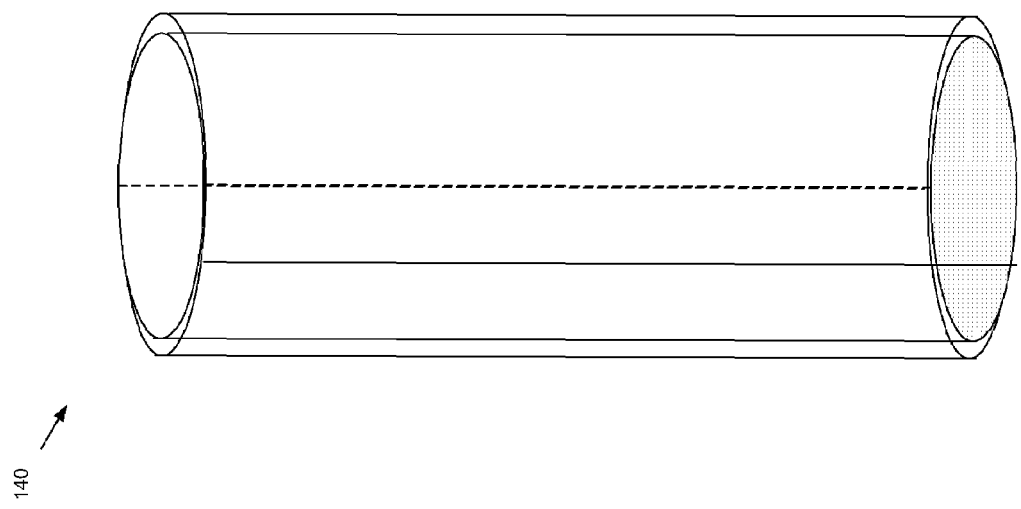
Figure 4C:
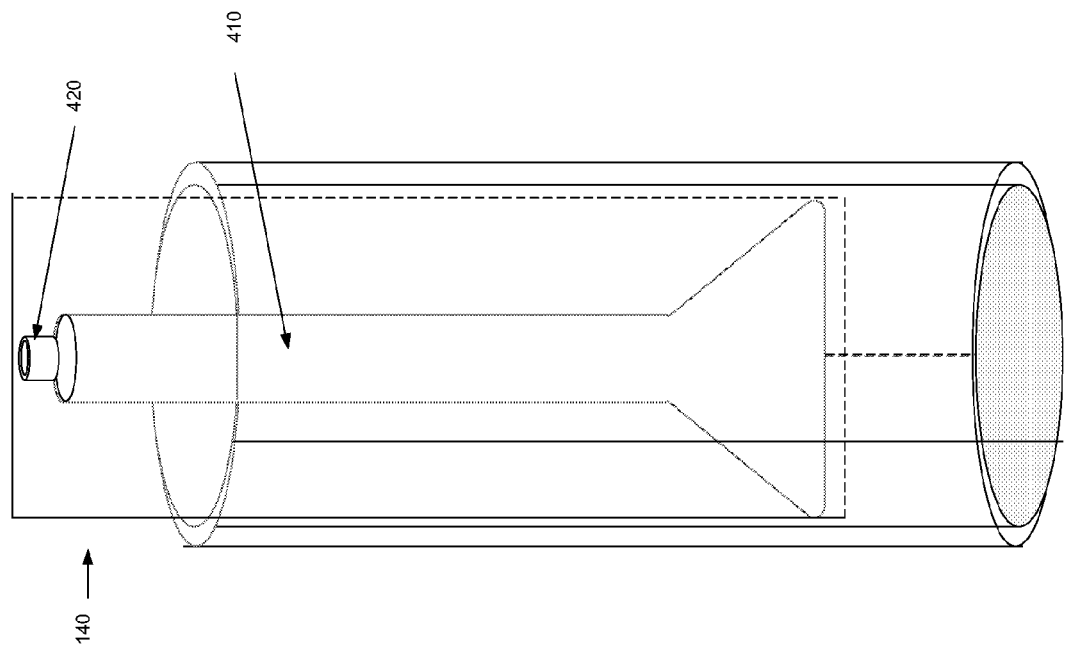
Figure 4B:
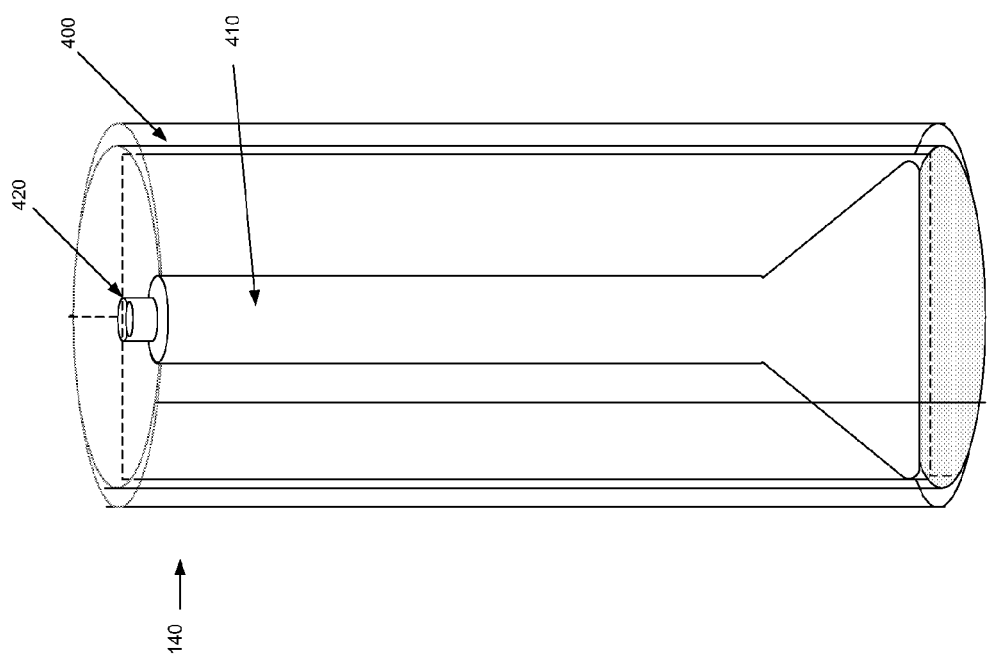

FIGS. 4A-4C illustrate perspective views of a sealed sleeve 140 mixing means 400. As shown by FIG. 4B, the sealed sleeve 140 defines a cavity for arrangement of mixing means 400. According to one embodiment of the present invention, mixing means 400 comprises a mixing paddle 410, with an associated coupling means 420 for coupling to, for example, a shaft of a mixer (not shown).

As used herein, the term "mixing means" relates to a mechanical system or components thereof, capable of transferring energy or motion to the materials housed in the mixing bag. The mixing means, which is isolated from the interior of the mixing tank by the exterior sleeve wall, serves to create turbulence and mixing while presenting no risk of contact with the mixture inside the vessel. Useful mechanical system components readily insertable into the sealed sleeve for transfer of energy to the components include elements such as, but not limited to, piezoelectric actuators, ultrasonic generators, rotation elements, swaying elements, blending elements, vibration elements, eductors, stirring elements, agitation elements, turbine elements, stator/rotor elements, impellers, helical mixing elements, and vortex generators. The mechanical system may be portable, or fixed mounted. Preferably, a component of the mechanical system comprises a rigid, detachable, support rod or shaft, which is insertable into the sealed sleeve. The support rod or shaft, having a proximal end closest to the upper wall 120 of mixing tank 100 and distal end farthest from upper wall 120 of mixing tank 100, may be enhanced by additional feature(s) such as paddles and/or blades. Moreover, the additional feature(s) such as paddle and/or blade, may be form fitted into the sleeve during a manufacturing process.

Figure 5A:
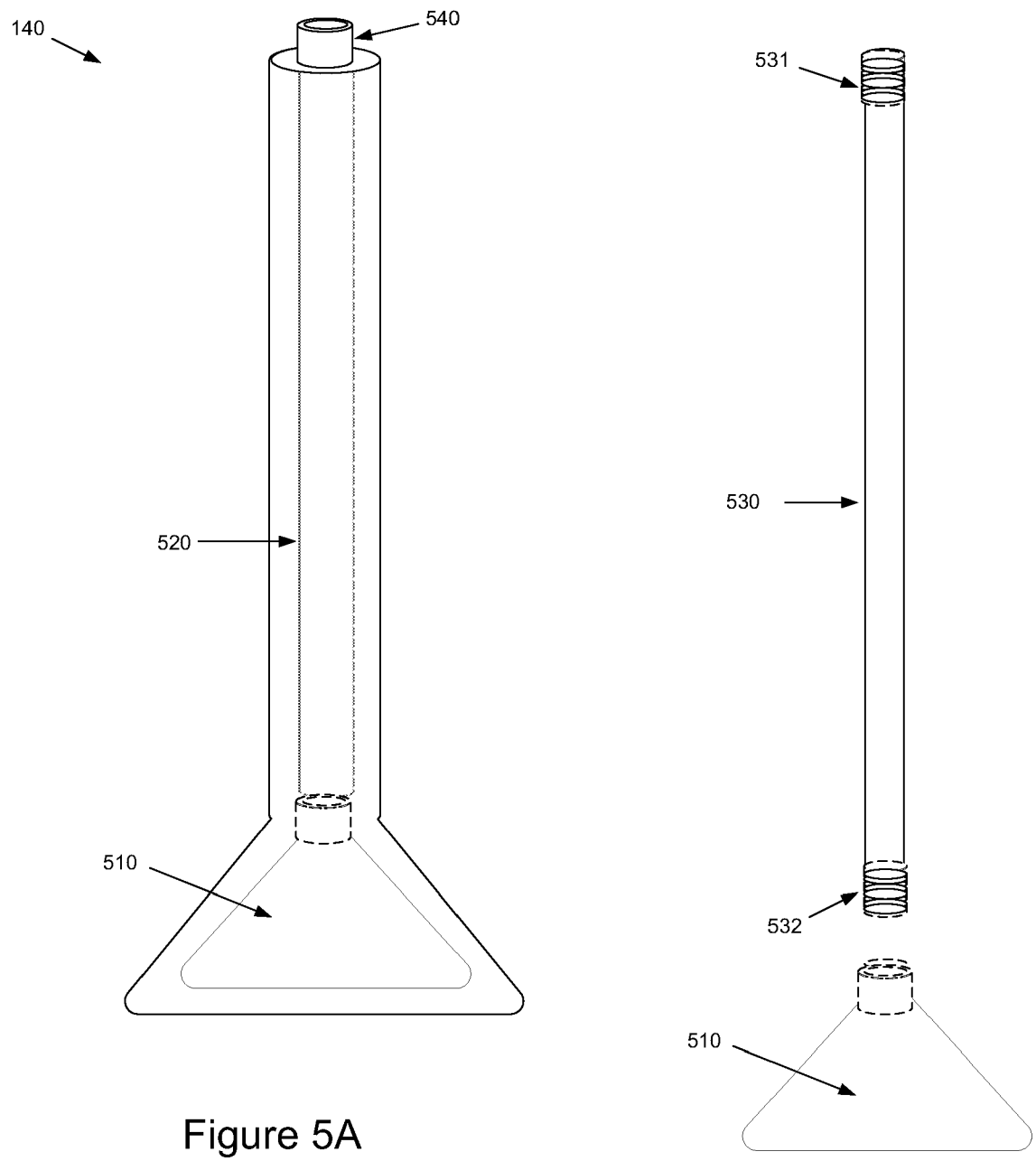
FIG. 5A illustrates a perspective view of sealed sleeve containing a mixing paddle and an exploded view of a mixing paddle and mixing shaft.
Figure 5C:
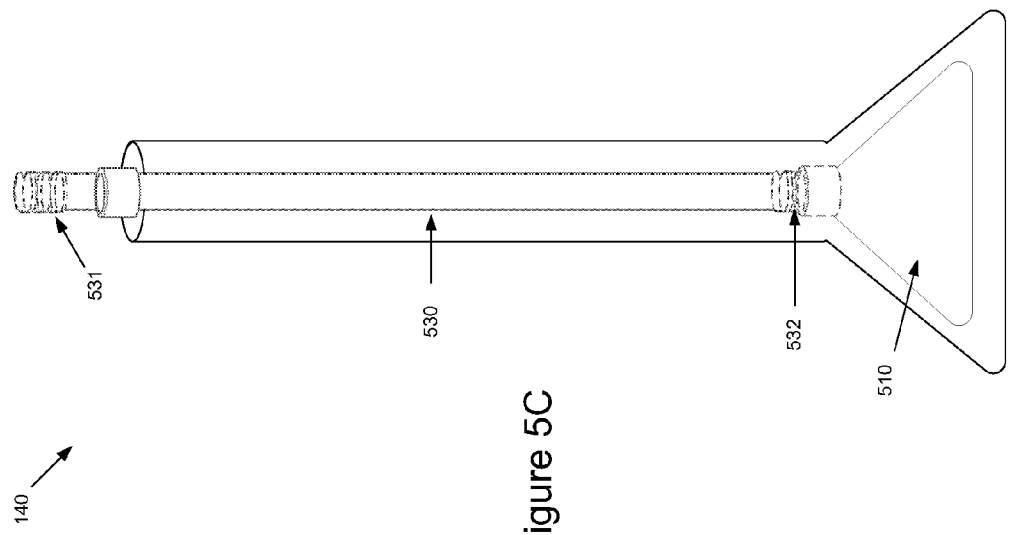
FIG. 5C illustrates the mixing shaft fully inserted into paddle-containing sealed sleeve of FIGS. 5A-5B, all according to a further embodiment of the present invention.
Figure 5B:
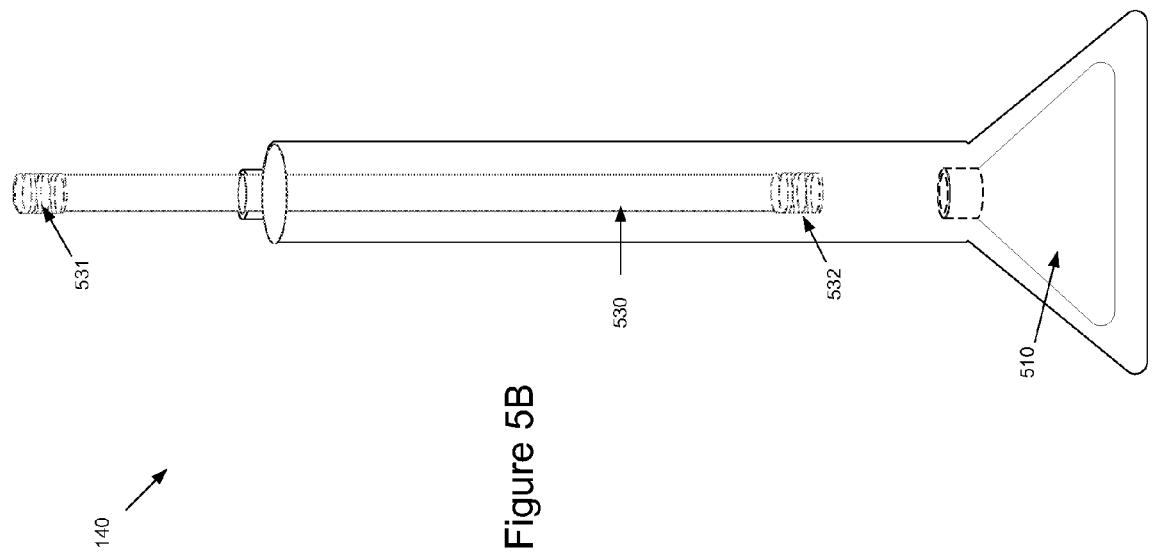
FIG. 5B illustrates the mixing shaft partially inserted into the paddle-containing sealed sleeve of FIG. 5A.

FIGS. 5A-5C illustrate the sealed sleeve 140 of mixing tank 100 and mechanical elements according to a preferred embodiment of the present invention. A sealed sleeve 140 comprises a paddle 510, hollow cavity 520, mixing shaft 530, and coupling guide 540. More specifically, FIG. 5A shows a sealed sleeve 140 having a paddle type device 510 form fitted therein during a manufacturing step. A hollow cavity 520 in the interior of sealed sleeve 140 provides for arrangement and coupling of a shaft- or rod-type component 530 to the paddle-type device 510. The support rod or shaft 530, having a proximal end 531 closest to the upper wall 120 of mixing tank 100 and distal end 532 farthest from upper wall 120 of mixing tank 100, couples to the paddle 510 at distal end 532. Such coupling may be made by any means readily available to one skilled in the art, at any time prior to a mixing step in a manufacturing process. The proximal end of the support rod 530 may couple, for example, to a mixer motor driver (not shown). The interior of hollow cavity 520 may be defined by the interior wall of the sealed sleeve 140. Alternatively, the interior of hollow cavity 520 may be defined by a separate integrated sleeve to provide additional protection and/or guard against potential punctures from a misfed or faulty rod or shaft. A coupling guide 540, sealed to the sleeve 140, serves as a rigid guide for insertion, arrangement and coupling of the support rod or shaft 530. The paddle-type device 510, support rod or shaft 530, and coupling guide 540 are preferably rigid, and may be formed from any material readily available to one skilled in the art, including, but not limited to, metals, alloys, composites, ceramics, composition (s) and material(s) described herein, and/or mixtures thereof. Preferably, the paddle device is absent of any sharp edges.

FIG. 5B shows insertion of a support rod 530 through a coupling guide 540 and into hollow cavity 520, while FIG. 5C shows the support rod 530 coupled to the paddle 510.

Preferably, the sealed sleeve is capable of a range of motion similar to an arm and hand in the glove of a glove or dry box. In a conventional dry box, the glove, which is preferably form fitted to the user's arm and hand, couples to the wall of the dry box, and isolates a user from an interior environment of the box. Although a portion of the glove contacts the contents in the box, the user is isolated from contacting the contents of the box by the glove, while a wide range of mobility is provided to the user's arm(s) and hand(s).

Figure 6:
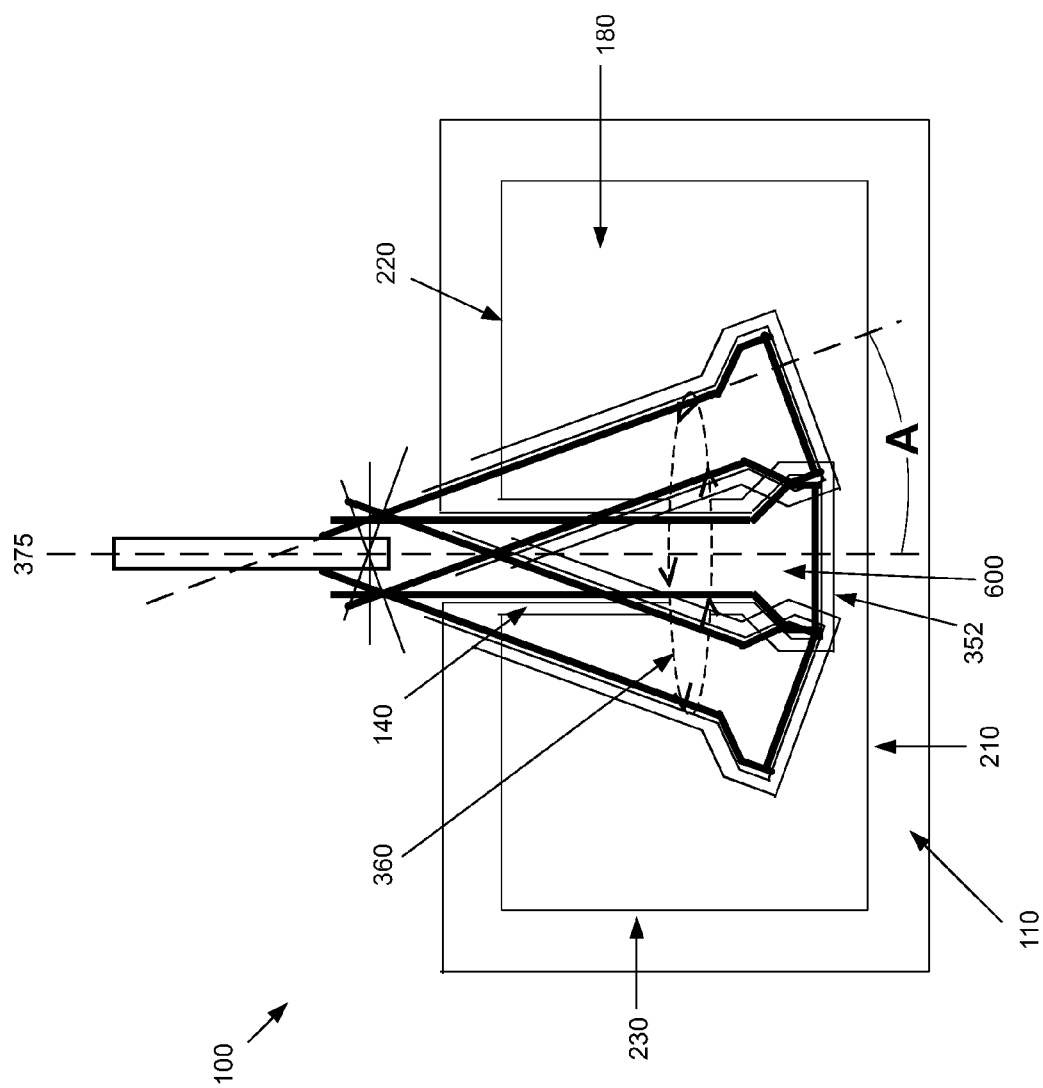
FIG. 6 illustrates a side view of a disposable mixing tank and associated sealed sleeve according to a further embodiment of the present invention, with the sealed sleeve shown in various positions of a 360 degree range of motion within the tank.

FIG. 6 serves to illustrate, a range of motion of a sealed sleeve 140, having a paddle 600 arranged therein by a form-fitting means, within a mixing tank 100. The paddle 600 may include one or more sections of manufacture. The interior portions of the bottom, top, and lateral tank walls 210, 220, 230 and exterior portion of the sealed sleeve wall 352 serve to define an interior volume 180 of the mixing tank 100 for housing components of a mixture, whether before or after a mixing process is performed. The sealed sleeve 140, comprising a paddle 600, moves within the mixing tank 100 at a nonzero angle A relative to a central vertical axis 375 of the tank 100, through a 360 degree range of motion (represented by dashed line 360) in a plane parallel to the mixing tank base 110, whereby through mechanical motion the paddle 600 at least partially combines the components contained within the interior volume 180 of the tank 100.

In one embodiment, the disposable mixing tank may be used for containment and storage of at least one component of the mixture, whereby the disposable mixing tank may store at least a first component for a period of time until at least a second component is added to the mixing tank for subsequent combining and mixing with the at least first component. Any of the first and second components may comprise multiple compositions as in a mixture or blend, or the first and second components may consist essentially of single compositions. Each component may be introduced into the mixing tank by one or more inlet openings.

In a still further embodiment, the present invention relates to a method of remixing, regenerating and/or revalidating a mixture, which over time has separated into two or more phases or components. The mixture, having been stored in a disposable mixing tank having a sealed sleeve therein, comprises two or more components prone to phase separations, including but not limited to emulsions, blends and suspensions (e.g., biological solutions comprising plasma, red cells, viruses, etc., or CMP slurries used in semiconductor manufacturing processes). The sleeve defines a sealed passageway for insertion or arrangement of mixing means therein. When the sleeve and mixing means are placed in a mixing mode, they serve to remix, regenerate, and/or revalidate the mixture in the mixing tank. Advantageously, the present invention serves to reduce the time required to regenerate a mixture because there is no downtime due to revalidation, as no transfer of materials is required.

In a further embodiment, the present invention relates to a kit including a disposable and collapsible tank having a sealed and collapsible sleeve disposed therein. The collapsible tank, having a storage/containment area defined by an interior wall of the collapsible tank and an exterior wall of the sleeve, is configured to house components prior to, during, and/or after a mixing process. The collapsible sleeve defines a sealed passageway for insertion or arrangement of mixing means therein. The mixing means is isolated from the interior of the mixing tank by the exterior sleeve wall, and hence does not contact the interior of the tank or components therein. The mixing means, when placed in a mixing mode, serves to mix components within the mixing tank. Preferably, the flexible sleeve includes a mixing rod shaft or other mixing components prearranged therein during a manufacturing process. The kit may further include packaging material and instructions or indicia located on the packaging material or inside the packaging material, and may optionally include ancillary components such as couplers, connectors and filters.

The figures shown herein thus far illustrate various embodiments of the disposable mixing tank in accordance with embodiments of the invention. However, it should be understood that the invention could be performed by embodiments of systems and apparatus other than those discussed with reference to the figures, and embodiments discussed with reference to the systems/apparatus could perform operations different than those discussed with reference to the figures.

A more detailed description of the different components of the disposable and flexible mixing tank 100 of FIG. 1 will now be described.

The tank walls 110, 120, 130 and sleeve walls 150 may be any type of flexible material for providing a flexible mixing apparatus (e.g., different types of plastics). For example, the walls 110, 120, 130, 150 may comprise heat-welded plastic films. In one embodiment, the walls 110, 120, 130, 150 are plastic films with a thickness in range of 5 microns to 500 microns (depending on the type of application). While the walls 110, 120, 130, 150 may be made from a number of different plastics, in one embodiment, the walls 110, 120, 130, 150 are made from a plastic that includes at least one material from the following group: polyethylene (PE), polypropylene (PP), polyvinyl chloride (PVC), polyethylene terephtalate (PET), polyetheretherketone (PEEK) polytetrafluoroethylene (PTFE) and polyfluoroalkoxy (PFA) derivates thereof. In a preferred embodiment, the mixing tank walls are manufactured from materials including at least one of ethylene vinyl acetate and metallocene polyethylene. In another embodiment, the walls 110, 120, 130, 150 comprise a stretchable material, having a deformation of less than approximately five percent when subjected to a tensile force of 100 gmf per inch (per 2.54 cm) of width. The tank and sleeve walls 110, 120, 130, 150 define the storage and/or mixing compartment that isolates components therein from the outside medium/environment. The films 110, 120, 130, 150 preferably also have a mechanical resistance such that the disposable mixing tank 100 may be used under pressure from the outside medium/environment. Preferably, the walls of the disposable mixing tank and sleeve are manufactured from similar materials, having similar thicknesses. In a preferred embodiment the wall thickness of each of the walls of the mixing tank and sleeve is about 200 microns.

In a further embodiment, the mixing tank walls 110, 120, 130 are substantially clear to allow for the viewing of the components and the mixture thereof, such that one skilled in the art may determine when the mix operation is complete based on viewing of the components. In one embodiment, the mixing tank walls include volumetric indicia for measuring the volume of the components therein.

In another embodiment, the disposable mixing tank 100 is a single-use apparatus. In particular, the mixing tank 100 is used to mix, at least partially, components contained therein. More preferably, the mixing tank is used to at least partially mix and store components therein. The result of the mixing of the components may be removed from the mixing tank 100 (as described in more detail below). Thereafter, the mixing tank 100 is discarded. Accordingly, there is no need to wash/sterilize the mixing tank 100 in preparation for subsequent uses. Moreover, because the mixing tank 100 is a single-use apparatus, the mixing tank 100 does not have the ongoing maintenance costs associated with conventional mixing devices.

The at least one outlet opening, 170, allows for draining the contents of the disposable mixing tank 100. While the mixing tank 100 is illustrated with separate inlet(s) 160 and outlet(s) 170, embodiments of the invention are not so limited. For example, in an embodiment, a single opening could be used for both loading and draining of components and/or mixtures.

In one embodiment, the inlet opening(s) 160, and the outlet opening(s) 170 include a base plate welded onto the internal or external face of the mixing tank walls 120, 130, such that one end of the opening emerges inside the wall 120, 130 and the other end emerges outside the wall 120, 130. Furthermore, the inlet openings 160 and the outlet openings 170 may be closed using a number of devices, such as tight plugs. In one embodiment, the diameters of the inlet openings 160 and the outlet openings 170 is dependent on the flow rate that a particular component is to be introduced into the mixing tank 100, and/or the admix operation that is to occur by movement of the mixing device arranged in the sealed sleeve 140. For a gas component, the gas inlet and outlet rate (or pressure) may be such that there is a sufficient homogenization of the components in the disposable mixing tank 100.

In a further embodiment, inlet opening(s) 160 and outlet opening(s) 170 may be used to introduce different types of probes into the mixing tank 100. For example, pH, pO2, temperature or pressure probes can be introduced into the mixing tank 100 through a number of inlet 160 and/or outlet 170 openings to check the status of the components and/or the result of the mixing of such components within the mixing tank 100.

The components to be stored in and the components that are to be admixed (mixed), at least partially together, during motion of the mixing device inside the flexible sleeve 140, may be in different phases (different types of solids, liquids and/or gases). For example, the solid components may be different types of powders. The liquid components may be in different organic phases and/or aqueous phases. The gases may include oxygen, air, nitrogen, argon, carbon dioxide, etc.

In one embodiment, the components are substantially homogenized. Moreover, the different components may or may not be soluble in reference to each other.

Any of a number of combinations of different components in different phases can be admixed in accordance with embodiments of the invention. For example, a first component in a solid phase may be mixed with a second component in a solid phase. A first component in a solid phase may be mixed with a second component in a liquid phase. In one such embodiment, a powder is suspended in a liquid component when the powder may be partially or totally insoluble in the liquid component. In an embodiment wherein the powder is totally soluble, the operation of the mixing tank 100 is such that the result is a homogenized solution of the powder and the liquid.

Further, a first component in a liquid phase may be mixed with a second component in a liquid phase. In one embodiment, the first liquid component may be partially soluble, totally soluble or totally insoluble with reference to the second liquid component. If at least one liquid component is at least partially insoluble in at least another liquid component, an emulsion is obtained after the mixing/stirring of the mixing tank 100. In an embodiment, if the liquid components are soluble in reference to each other, the operation of the mixing tank 100 is such that the result is a homogenized solution of the two different liquid components.

A first component in a liquid phase may be mixed with a second component in a gas phase. The gas may be inert or may react with at least one component of the liquid component. For example, a gas (that is relatively reactive under the desired conditions) may be oxygen or carbon dioxide when culturing cells or microorganisms or to provide for an oxidation reaction.

The width/diameter of sealed sleeve 140, and the width/diameter of the inlet(s) 160 and outlet(s) 170, are dependent on the size of the mixing tank 100 and on the identity of the components to be mixed and/or transferred. The width/diameter and height of sealed sleeve 140 must allow for the arrangement of mixing means therein. Moreover, the dimensions of the sealed sleeve 140 are based on the size of the mixing tank 100 and the physical characteristics of the components to be mixed. Examples of the type of characteristics on which the diameter of the sleeve 140 is dependent include viscosity, granulometry, density, thixotropy and rheoscopy.

In one embodiment, the mixing tank 100 also includes at least one valve to allow for a release mechanism in the event that pressure builds up within the mixing tank 100 because of the mixing/rotation operation.

In a further embodiment, the disposable mixing tank 100 may comprise a support frame 115, as shown in FIG. 1. The support frame may surround the disposable mixing tank 100 and can couple to the mixing bag 100, through one of a number of connection apparatus (e.g., a clip, a hook, etc., not shown). The frame may additionally function as support for mixing means and related ancillaries. Accordingly, the support frame supports the mixing tank 100, so as to maintain a sufficient tension during loading of components into the mixing tank as well as during the mixing of the components contained therein.

Figure 7:
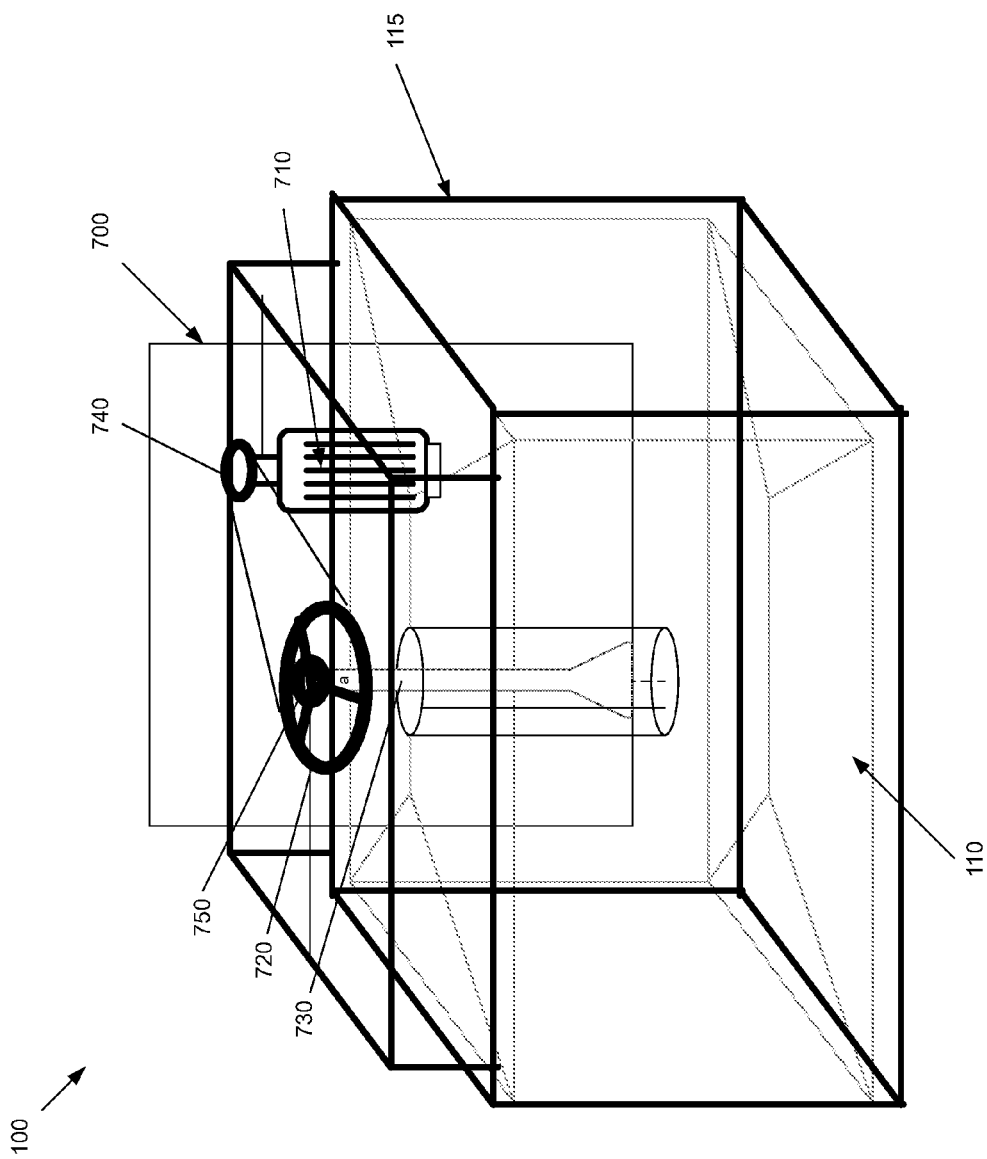
FIG. 7 illustrates a perspective view of a sealed sleeve-containing disposable mixing tank and mixing means supported by a frame, all according to a further embodiment of the present invention.

FIG. 7 illustrates disposable mixing tank 100, comprising mixing means 700, whereby both mixing tank 100 and mixing means 700 are supported by a frame 115. Motor-wheel driver 710 couples to rotation wheel 720, which couples to mixing stick 730 through bearings 740, 750. The motor-wheel driver 710 may communicate directly with a processor to execute machine-readable instructions for controlling the rotation of the mixing stick 730, including the number of turns, the rate of rotation, the angle of rotation, and how far to turn for a given rotation, as described in more detail below in conjunction with the description of the flow diagram 800 of FIG. 8.

In a further embodiment, the disposable mixing tank of the present invention may further comprise a secondary containment system for containment of materials, which may leak from the tank during storage, processing, and/or transfer of such materials into and/or out of the mixing tank. The secondary containment system may be fixed or portable. Further, the appropriate secondary containment system for use with the disposable mixing tank may be readily determined by one skilled in the art.

In a further embodiment, the disposable mixing tank of the present invention may further comprise external heating and/or cooling means for controlling the temperature of components in the disposable mixing tank. The secondary containment system may serve as housing for a fluid that conducts heat into or out of the disposable mixing tank, such as with heating and cooling baths. Alternatively, the heating and/or cooling means may envelope the exterior of the disposable mixing tank or a portion thereof as in, for example, heating jackets, heating and cooling tanks, heat exchangers, chillers, and fluid cooling systems. As a still further alternative, the mixing tank may comprise a liner, exterior to the outer walls of sealed cavity 140 and mixing tank 100. The liner preferably envelops at least a portion of the mixing tank and provides a sealed gap or space between the liner and exterior walls of sealed cavity 140 and mixing tank 100. The gap or space is useful for containing fluids having heat and/or cooling capacities. Preferably, the heating and/or cooling fluid contained therein is circulatable in the gap or space by circulation means.

Figure 8:
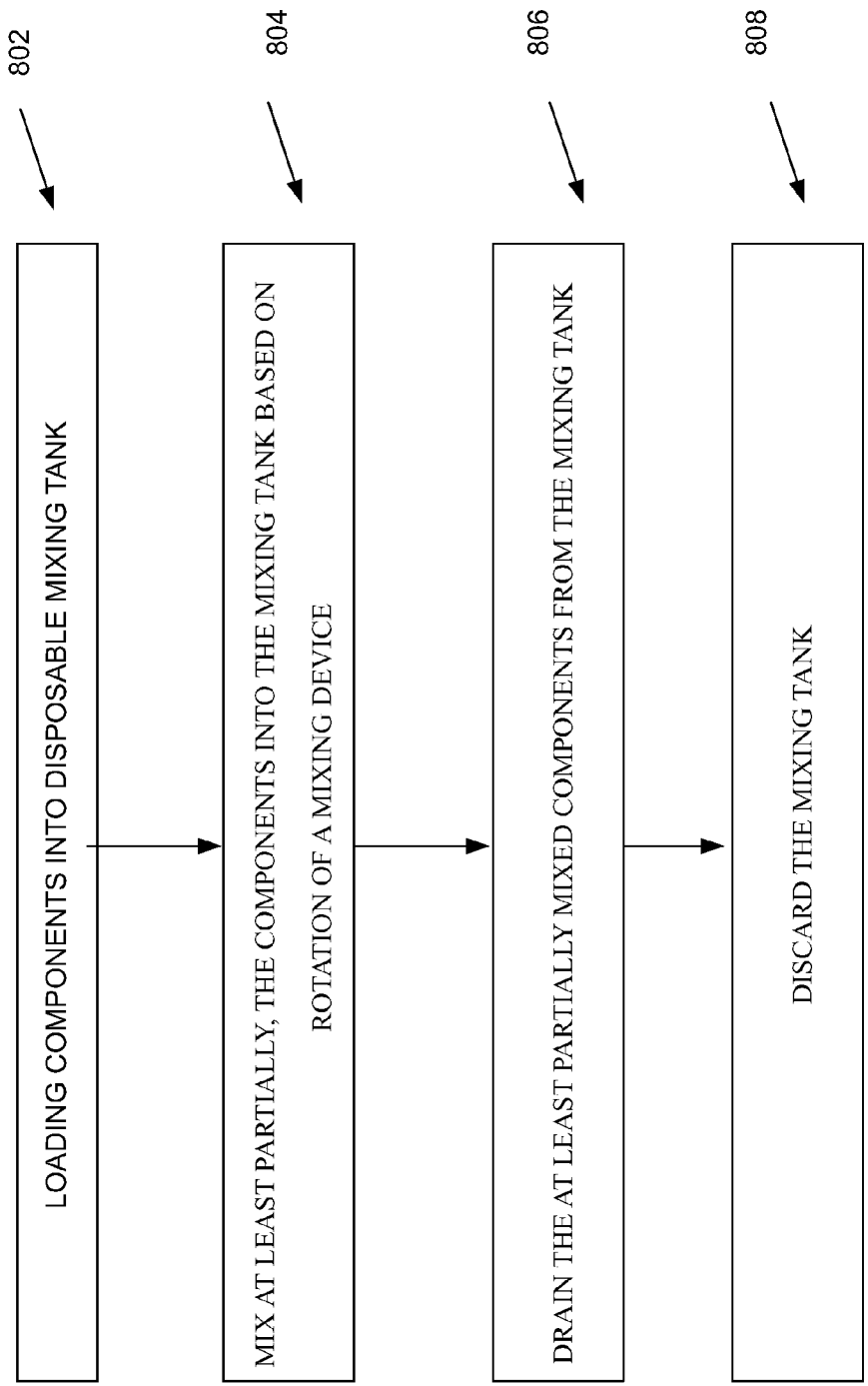
FIG. 8 illustrates a flow diagram for the steps of a method for mixing components according to a further embodiment of the invention.

FIG. 8 illustrates a flow diagram for the steps of a method for mixing components, according to a further embodiment of the invention. In a first step described in block 802, components are loaded into mixing tank 100 through an inlet 160. The inlet 160, or multiple inlets (not shown), may be opened in an order that is in accord with a mixing protocol for the components to be loaded into mixing tank 100. For example, a more homogenous solution may be derived for three components if a first component and a second component are mixed, followed by the mixing of the third component into the mixture of the first component and the second component.

In the first step described in block 802, the components may be loaded simultaneously or based on a mixing protocol or instructions from a CPU. As described above, the number of inlet openings 160 allow for the introduction of components ("raw materials" or "reactants") to be mixed within the mixing tank 100. Control continues at a second step described in block 804.

The loading operation as described in the first block 802, while described such that the operations of the second block 804 are subsequent to the operations of the block 802, is not so limited in all embodiments. For example, as described above, different inlets may be opened at different times during the mixing of the components in order to follow a mix protocol for a given set of components. Accordingly, the opening of an inlet for filling may follow a first mix operation, which is followed by a second mix operation.

In a second step described in a second block 804, the components loaded into the mixing tank 100 are mixed, at least partially, based on rotation or other motion of the mixing device as shown in FIG. 7. The mixing of the components may be performed or controlled by an individual and/or a control apparatus (not shown). The mixing of the components may be carried out by a number of rotations of the mixing means 700, wherein one rotation includes rotating at least a 360 degree turn. In one embodiment, the range of motion through the 360 degree rotation is in a plane parallel to the mixing tank base 110.

In an embodiment to generate a homogenous solution, the rotation of mixing means 700 in the mixing tank 100 continues until the components are approximately homogenized. In an embodiment that includes mixing a liquid and a powder that is at least partially insoluble, the rotation of mixing means 700 continues until the powder is suspended in the liquid.

Moreover, as described above, a number of open passage operations and mix operations may occur in order to follow a given mix protocol. Accordingly, a number of mix operations may occur until the different components are mixed, at least partially, into the final resulting component. Control continues with a third step described in a third block 806.

In a third step described in the third block 806, the at least partially mixed components are drained from the mixing tank 100. In one embodiment, the mixing tank 100 is positioned such that when a plug type device is removed or a valve is opened, mixed components drain from an outlet 170. The drain operation may be facilitated as desired. For example, when the component is a viscous solution having a slow flow, the drain operation may be facilitated through a number of operations. In one embodiment, the drain operation is facilitated by an increase in pressure initiated by introducing a gas into an inlet opening(s) 160. Control continues with a fourth step described in a fourth block 808.

In the fourth step described in the fourth block 808, the mixing tank 100 is discarded. In particular, the mixing tank 100 is discarded after a single use. Accordingly, the washing/sterilizing operations as well as the maintenance associated with conventional mixing devices are not needed. Moreover, as described, embodiments of the invention reduce the amount of human contact with the components (which may be hazardous, dangerous and/or infectious) that are to be mixed as part of and during the mixing of such components.

Thus, a method, apparatus and system for different embodiments for mixing solids, liquids and/or gases have been described.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A mixing apparatus comprising:
   a hollow mixing container having at least one interior wall;
   a mixing paddle adapted to engage a support rod mechanically coupleable to receive kinetic energy from a kinetic energy source, the mixing paddle having at least one widened paddle portion that is wider than a nominal diameter or cross-sectional width of the support rod;
   a coupling guide joined to the mixing container, the coupling guide defining an aperture sized to permit pivotal arrangement of the support rod between the kinetic energy source and the mixing container;
   an integral sleeve sealingly and permanently welded proximate the coupling guide aperture to any of the container and the coupling guide, the sleeve having a closed end protruding into the interior of the hollow container, having at least one exterior wall, and defining a cavity containing the mixing paddle, the cavity having at least one widened cavity portion disposed about the at least one widened paddle portion;

a drain port associated with the mixing container; and at least one inlet port associated with the mixing container;

wherein (i) the at least one interior wall of the mixing container and the at least one exterior wall of the sleeve encloses a volume, (ii) the sleeve serves as an isolation barrier between the volume and the mixing paddle, and (iii) the mixing container is adapted to permit pressure-assisted draining of any contents thereof.

2. The mixing apparatus of claim 1, wherein the mixing container comprises a mixing bag comprising a substantially transparent polymeric film material.

3. The mixing apparatus of claim 1, wherein said at least one inlet port is adapted for coupling to a source of pressurized gas.

4. The mixing apparatus of claim 3, coupled in fluid-receiving relationship to a source of pressurized gas.

5. The mixing container of claim 1, wherein the sleeve is sized and shaped to be substantially form-fitting around the mixing paddle.

6. The mixing container of claim 1, wherein any of the mixing container and the sleeve comprises a polymeric film.

7. The mixing container of claim 1, wherein each of the mixing bag and the sleeve comprises a polymeric film, and the polymeric film of the mixing bag has substantially the same composition as the polymeric film of the sleeve.

8. A mixing system including the mixing apparatus of claim 1 coupled to a kinetic energy source.

9. A mixing method employing a mixing apparatus including (i) a kinetic energy source, (ii) a hollow mixing bag having a flexible integral sleeve joined thereto with a closed end of the sleeve protruding into the mixing bag, and having an associated drain port and an associated at least one inlet port, and (iii) a mixing paddle enveloped by the sleeve and adapted to receive a support rod coupleable to the kinetic energy source, wherein at least one interior wall of the bag and an exterior wall of the sleeve defines an interior volume, and the sleeve serves as an isolation barrier between the interior volume and the mixing paddle, the method comprising the steps of:

supplying at least two components of a mixture to the interior volume;

engaging the support rod between the kinetic energy source and the mixing paddle;

mixing the at least two components by moving the enveloped mixing paddle in a closed curvilinear path within the interior volume without continuous rotation of the support rod about a longitudinal axis defined by the support rod to combine the at least two components and form said mixture;

supplying pressurized gas to the container via any inlet port of the at least one inlet port; and draining at least a portion of said mixture via said drain port.

10. The method of claim 9, wherein the moving step comprises moving the mixing element within the tank through a defined path at a nonzero angle relative to a substantially central vertical axis of the tank.

11. The method of claim 9, wherein the closed curvilinear path comprises a substantially circular path.

12. The method of claim 9, wherein the mixing bag comprises a coupling guide defining an aperture sized and shaped to permit pivotal arrangement of the support rod between the kinetic energy source and the mixing bag, and the mixing step includes pivotally moving support rod through the coupling guide to direct the mixing paddle in the closed curvilinear path.

13. The method of claim 9, wherein said supplying of at least two components to the interior volume is performed through any of the at least one inlet port.

14. A mixing apparatus comprising:

a hollow mixing container having at least one interior wall;

a mixing paddle adapted to engage a support rod mechanically coupleable to receive kinetic energy from a kinetic energy source, the mixing paddle having at least one widened paddle portion that is wider than a nominal diameter or cross-sectional width of the support rod;

a coupling guide joined to the mixing container, the coupling guide defining an aperture sized to permit pivotal arrangement of the support rod between the kinetic energy source and the mixing container;

an integral sleeve sealingly and permanently welded proximate the coupling guide aperture to any of the container and the coupling guide, the sleeve having a closed end protruding into the interior of the hollow container, having at least one exterior wall, and defining a cavity containing the mixing paddle, the cavity having at least one widened cavity portion disposed about the at least one widened paddle portion;

a thermal exchange vessel arranged to contain a thermal exchange fluid in thermal communication with at least a portion of the mixing container; and a thermal exchange element disposed in at least intermittent thermal communication with the thermal exchange fluid;

wherein the at least one interior wall of the mixing container and the at least one exterior wall of the sleeve encloses a volume, and the sleeve serves as an isolation barrier between the volume and the mixing paddle.

15. The mixing apparatus of claim 14, wherein the mixing container comprises a mixing bag comprising a substantially transparent polymeric film material.

16. The mixing apparatus of claim 14, wherein the thermal exchange vessel comprises a secondary containment vessel containing at least a substantial portion of said mixing container.

17. The mixing apparatus of claim 14, wherein the thermal exchange vessel substantially envelops the mixing container.

18. The mixing apparatus of claim 14, wherein the thermal exchange vessel is disposed exterior to the mixing container.

19. The mixing apparatus of claim 14, wherein said the thermal exchange vessel and said mixing container define a substantially sealed gap or space therebetween adapted to contain said thermal exchange fluid.

20. The mixing apparatus of claim 14, further comprising a circulation element adapted to circulate the thermal exchange fluid in or through the thermal exchange vessel.

21. The mixing apparatus of claim 14, further comprising a temperature control element, wherein said apparatus is adapted to alter any of temperature and circulation of said thermal exchange fluid responsive to a signal provided by said temperature control element.

22. The mixing apparatus of claim 14, further comprising a temperature control element controlling temperature of said mixture by affecting any of temperature and circulation of said thermal exchange fluid.

23. The mixing container of claim 14, wherein the sleeve is sized and shaped to be substantially form-fitting around the mixing paddle.

24. The mixing container of claim 14, wherein any of the mixing container and the sleeve comprises a polymeric film.

25. The mixing container of claim 14, wherein each of the mixing bag and the sleeve comprises a polymeric film, and the polymeric film of the mixing bag has substantially the same composition as the polymeric film of the sleeve.

26. A mixing system including the mixing apparatus of claim 14 coupled to a kinetic energy source.

27. A material processing method employing a mixing apparatus including (i) a kinetic energy source, (ii) a hollow mixing bag having a flexible integral sleeve joined thereto with a closed end of the sleeve protruding into the mixing bag, and (iii) a mixing paddle enveloped by the sleeve and adapted to receive a support rod coupleable to the kinetic energy source, wherein at least one interior wall of the bag and an exterior wall of the sleeve defines an interior volume, and the sleeve serves as an isolation barrier between the interior volume and the mixing paddle, and (iv) a thermal exchange vessel arranged to contain a thermal exchange fluid in thermal communication with at least a portion of the mixing container, the method comprising the steps of:

supplying at least two components of a mixture to the interior volume;

engaging the support rod between the kinetic energy source and the mixing paddle;

mixing the at least two components by moving the enveloped mixing paddle in a closed curvilinear path within the interior volume without continuous rotation of the support rod about a longitudinal axis defined by the support rod to combine the at least two components and form said mixture; and controlling temperature of said mixture by altering any of temperature and circulation of said thermal exchange fluid.

28. The method of claim 27, wherein the moving step comprises moving the mixing element within the tank through a defined path at a nonzero angle relative to a substantially central vertical axis of the tank.

29. The method of claim 27, wherein the closed curvilinear path comprises a substantially circular path.

30. The method of claim 27, wherein the mixing bag comprises a coupling guide defining an aperture sized and shaped to permit pivotal arrangement of the support rod between the kinetic energy source and the mixing bag, and the mixing step includes pivotally moving support rod through the coupling guide to direct the mixing paddle in the closed curvilinear path.

31. The method of claim 27, wherein the thermal exchange vessel comprises a secondary containment vessel containing at least a substantial portion of said mixing container.

32. The method of claim 27, wherein the thermal exchange vessel substantially envelops the mixing container.

33. The method of claim 27, wherein the thermal exchange vessel is disposed exterior to the mixing container.

34. The method of claim 27, further comprising circulating said thermal exchange fluid in or through the thermal exchange vessel.

35. The method of claim 27, further comprising altering any of temperature and circulation of said thermal exchange fluid responsive to a signal provided by a temperature control element.

36. The method of claim 27, further comprising controlling temperature of said mixture by affecting any of temperature and circulation of said thermal exchange fluid.

\* \* \* \* \*

UNITED STATES PATENT AND TRADEMARK OFFICE
CERTIFICATE OF CORRECTION

PATENT NO.          : 7,431,494 B2
APPLICATION NO. : 11/831735
DATED                    : October 7, 2008
INVENTOR(S)         : Jean-Pascal Zambaux It is certified that error appears in the above-identified patent and that said Letters Patent is hereby corrected as shown below:

Title page item [74] Attorney, Agent, or Firm, "Intellectual Property Technology Law" should be -- Intellectual Property/Technology Law --.

Signed and Sealed this

Twenty-fourth Day of February, 2009

JOHN DOLL
*Acting Director of the United States Patent and Trademark Office*